United States Patent
Chou et al.

(10) Patent No.: US 9,261,499 B2
(45) Date of Patent: Feb. 16, 2016

(54) BIOCHEMICAL DETECTION UNIT AND BIOCHEMICAL DEVICE HAVING THE SAME

(75) Inventors: Chung-Cheng Chou, Lujhu Township, Taoyuan County (TW); William Wang, Taoyuan (TW)

(73) Assignee: Crystalvue Medical Corporation, Gueishan, Taoyuan (TW)

( * ) Notice: Subject to any disclaimer, the term of this patent is extended or adjusted under 35 U.S.C. 154(b) by 676 days.

(21) Appl. No.: 13/045,218

(22) Filed: Mar. 10, 2011

(65) Prior Publication Data
US 2012/0231531 A1    Sep. 13, 2012

(30) Foreign Application Priority Data
Mar. 10, 2010   (TW) .............................. 99106966 A

(51) Int. Cl.
G01N 33/543   (2006.01)
G01N 27/12    (2006.01)

(52) U.S. Cl.
CPC ........ *G01N 33/54306* (2013.01); *G01N 27/126* (2013.01)

(58) Field of Classification Search
CPC .................... G01N 27/126; G01N 33/54306
USPC ...................................... 435/287.2
See application file for complete search history.

(56) References Cited

U.S. PATENT DOCUMENTS

| 5,891,649 A * | 4/1999 | Kidwell et al. ............ 435/7.9 |
| 2006/0205060 A1 | 9/2006 | Kim et al. |
| 2009/0221089 A1* | 9/2009 | Kimura .................. 436/172 |
| 2011/0223689 A1* | 9/2011 | Bailey .................... 436/506 |

FOREIGN PATENT DOCUMENTS

CN    101152650 A    4/2008

* cited by examiner

*Primary Examiner* — Gautam Prakash
(74) *Attorney, Agent, or Firm* — Patterson & Sheridan, LLP

(57) ABSTRACT

A biochemical detection unit for detecting a sample and a biochemical device having the biochemical detection unit and a releasing unit are provided. The biochemical detection unit includes a photoconductor plate, a receptor, and a resistance sensing component. The receptor specifically binds to the sample so that the illumination projected on the photoconductor plate will change to vary the resistance value of the photoconductor of the photoconductor plate.

14 Claims, 12 Drawing Sheets

BIOCHEMICAL DETECTION UNIT AND BIOCHEMICAL DEVICE HAVING THE SAME

BACKGROUND OF THE INVENTION

1. Field of the Invention

The present invention generally relates to a biochemical detection unit. Particularly, the present invention relates to a biochemical detection unit having a photoconductor and a biochemical device having the biochemical detection unit.

2. Description of the Prior Art

Generally speaking, biochips refer to applicable biochemical analysis products manufactured with materials such as glass, silicon chip, or plastic through microelectronics or/and micromechanical industrial technologies, wherein the intended target subjects of the biochips may include genes, proteins, cell structures, or any other separable compounds from the environment. The main characteristic of biochip technologies lies in the high credibility and accuracy levels of its analyses, the fast analysis speed, the low usage of samples and reagents in analyses, and the procurement capabilities of holistic (parallel) experimental data.

The conceptual source of biochips originated in the late '80s of the 20th century where many western research units realized that the development and application of biochips—products realized from the integration of microelectronics, micromechanics, life science, and bioinformation—would inevitably cause a biotechnological revolution in the 21th century. Overall, although international biochip research is still in the early developmental stages, several important and major achievements have already been accomplished, such as gene chips (DNA chip, Microarray), protein chips, Microfluidics, and Lab-on-a-chip. Among these different research branches, gene chip is furthest along in development. Presently, biochips mentioned in academic research or in the biotechnology industry refer mostly to gene chips.

Gene chips can be classified into two types depending on the DNA sample preparation methods. The first type is prepared by light-directed synthesis, developed by Affymetrix Incorporated, which is a combination of chemical synthesis and photolithography. The second type is prepared by contact printing, developed by Stanford University, which involves fixating in high density pre-synthesized DNA to glass slides with robotic arms at high speeds. This form of high density chip formation is commonly known as Microarray and is currently the most popular industry.

International Standards of Gene Microarray involves spotting the probes onto the surface of a chemically coated glass slide in manner of high density so that a typical amount in the range of thousands or tens of thousands of DNA or cDNA are fixated thereof, while the sample for testing is the nucleic acids of the cDNA (target). The glass slide and the sample then undergo hybridization. Due to the fact that DNA double helices have specific complementary characteristics that are analogous to a zipper's characteristic, the targeted nucleic acids in the sample will bind to the cDNA microarray at the spotting of the probe containing the complementary nucleic acid sequence by means of hybridization. Then, after washing away any unhybridized nucleic acids in the sample, the spots where hybridization had occurred may be recorded through utilizing labeling objects (such as fluorescence, radiation, enzyme reaction colorization) contained in the probes for further scanning and analysis.

Since there may be thousands or tens of thousands of gene spots on a biochip, the colored pattern formed by the labeling object requires proper recordation and comparison. As well, the colored pattern may change according to the duration of reaction. Therefore, a great challenge in Microarray technology is comparison of the color variance and the determination of hybridization spots. Based on the mentioned challenges above, the present invention provides a reasonable and effective design to overcome said challenges.

SUMMARY OF THE INVENTION

It is an object of the present invention to provide a biochemical detection unit. When a sample binds to the receptor, through integrating a photoconductor and a receptor, the illumination on a photoconductor plate will change in response to being covered by the sample. Since the illumination changes, a resistance sensing component can then sense a change in the resistance value of the photoconductor of the photoconductor plate so that the bond between the sample to the specific receptor can be precisely detected. In this manner, the present invention can avoid errors in the comparison of color variations.

It is another object of the present invention to provide a biochemical device which can release at least one agent to react with the receptor to cause the variation in resistance value. The at least one agent includes first affinity agents consisting of a reaction portion and a binding portion. The binding portion allows the first affinity agent to bind specifically to a receptor to which the sample is bound. In this manner, the present invention can prevent a false positive reaction from occurring.

It is another object of the present invention to provide a biochemical device which has quantitative analysis capabilities. Through the disposition of a primary channel, a sub-channel, and a sampling unit, the sample can be dispersed to different reaction areas in order to prevent oversaturation that would have resulted from the sample gathering in certain reaction areas.

The present invention provides a biochemical detection unit for detecting a sample. The biochemical detection unit includes a photoconductor plate, a receptor, and a resistance sensing component. The receptor is disposed on the photoconductor plate and includes an affinity site to which the sample can bind to thereof specifically. A gap exists between the affinity portion and the photoconductor plate. In other words, the affinity portion and the photoconductor plate is not directly connected to each other.

The resistance sensing component of the present invention is electrically coupled to the photoconductor plate and can detect changes in the illumination on the photoconductor plate that are caused in response to the bonds formed by the sample to the receptors. The illumination changes affect the resistance value of the photoconductor. As a result, the resistance sensing component is provided to sense the variation in resistance value of the photoconductor plate.

DETAILED DESCRIPTION OF THE PREFERRED EMBODIMENT

The biochemical detection unit of the present invention can detect samples including amino acid monomers, amino acid residues, amino acid polypeptides, proteins, organic compounds, inorganic compounds, metal compounds (including oxides, sulfides, nitro compounds), metal alloys, monomers of organic polymers, and various other organic polymers.

Figure 1A:
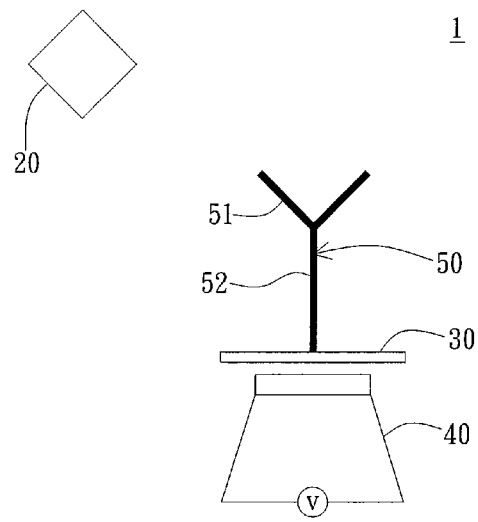
FIG. 1A is a schematic view of the biochemical detection unit.

As shown in FIG. 1A, a biochemical detection unit 1 of the present invention for detecting a sample 20 includes a photoconductor plate 30, a receptor 50, and a resistance sensing component 40. The receptor 50 is preferably disposed on the photoconductor plate 30 and is preferably an Immunoglobulin (Ig). However, in other embodiments, the receptor 50 may be of other amino acid residues, such as an amino acid residue which can bind specifically to the sample 20. As shown in the embodiment of FIG. 1A, the receptor 50 has an affinity site 51 and a linking portion 52, wherein the affinity site 51 can allow the sample 20 to bind specifically to thereof. The term "bind specifically" mentioned herein refers to the amino acid fragments of the affinity site 51 binding through intermolecular affinity bonds such as van der Waals forces and hydrogen bond forces. In the embodiment shown in FIG. 1A, the linking portion 52 is preferably a Fc fragment of an Immunoglobulin, wherein the linking portion 52 is also preferably linked to the photoconductor plate 30 through chemical bonds. However, in other embodiments (not shown), the linkage between the linking portion 52 and the photoconductor plate 30 may be through intermolecular affinity bonds such as hydrogen bonds and van der Waals forces. As such, a distance between the affinity site 51 and the photoconductor plate 30 exists, wherein the distance is preferably between 0.1 μm~0.1 cm, and even better if the distance is between 1 μm~1 mm or 10 μm~100 μm.

As shown in the embodiment of FIG. 1A, the biochemical detection unit 1 includes the resistance sensing component 40, wherein the resistance sensing component 40 is electrically coupled to the photoconductor plate 30 for sensing variations in the resistance value of the photoconductor plate 30. The resistance sensing component 40 is preferably a Volt/Ohm Meter (VOM) or any other apparatuses or devices for use in measuring variations in resistance values.

Figure 1B:
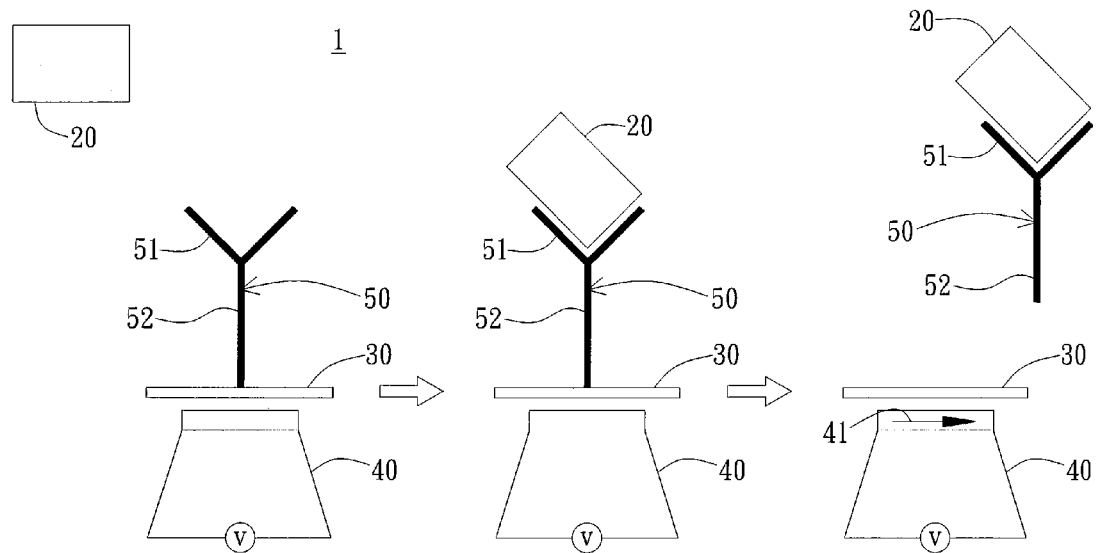
FIG. 1B is a schematic view of the reaction in the biochemical detection unit.

As shown in the embodiment of FIG. 1B, the receptor 50 may be designed to allow affinity binding specifically to the sample 20. Furthermore, the receptor 50 may be designed to produce a conformational change in response to the affinity bonds formed with the sample 20 by weakening the affinity bonds between the linking portion 52 and the photoconductor plate 30. The weakened affinity bond between the linking portion 52 and the photoconductor plate 30 will allow the linking portion 52 to easily separate from the photoconductor plate 30. When the receptor 50 together with the sample 20 separates from the photoconductor plate 30, the illuminated area of the photoconductor plate 30 increases so that the resistance sensing component 40 senses a variation in resistance value of the photoconductor plate 30. According to different photoconductor plates 30, the resistance value may be designed to decrease or increase according to a degree of increase in the illumination so that the resistance sensing component 40 can produce a resistance change signal 41. In other words, the resistance change signal 41 represents a change in the resistance value, and not necessarily to just a simple decrease or increase in the resistance value.

The photoconductor of the present invention is defined as a material capable of converting electromagnetic radiation to electric current, wherein the electromagnetic radiation usually refers to ultraviolet light (UV), visible light, and infrared light. In general, when these types of material hold static electricity, the static electricity may be converted to electric current after the material has been illuminated by light having a specific wavelength. In other words, these materials make good insulators in darkness, and excellent electrical conductors under illumination. The photoconductor of the photoconductor plate 30 of the present invention primarily can be classified into organic photoconductors and inorganic photoconductors. The organic photoconductors can be selected from polyvinylcarbazole, phthalocyanine complex, azo compound, squalene compound, and a mixture thereof. The inorganic photoconductors can be selected from Se, Se/Te alloy, CdS, ZnO, PbS, InSb, and a mixture thereof. The photoconductor plate 30 of the present invention can be composed of purely organic photoconductors, purely inorganic photoconductors, or a mixture of organic and inorganic photoconductors thereof. In addition, the manner of mixing the organic and inorganic photoconductors includes, but is not limited to, layering, mix-crystallization, coating, chemical vapor deposition, and other related methods.

Figure 2A:
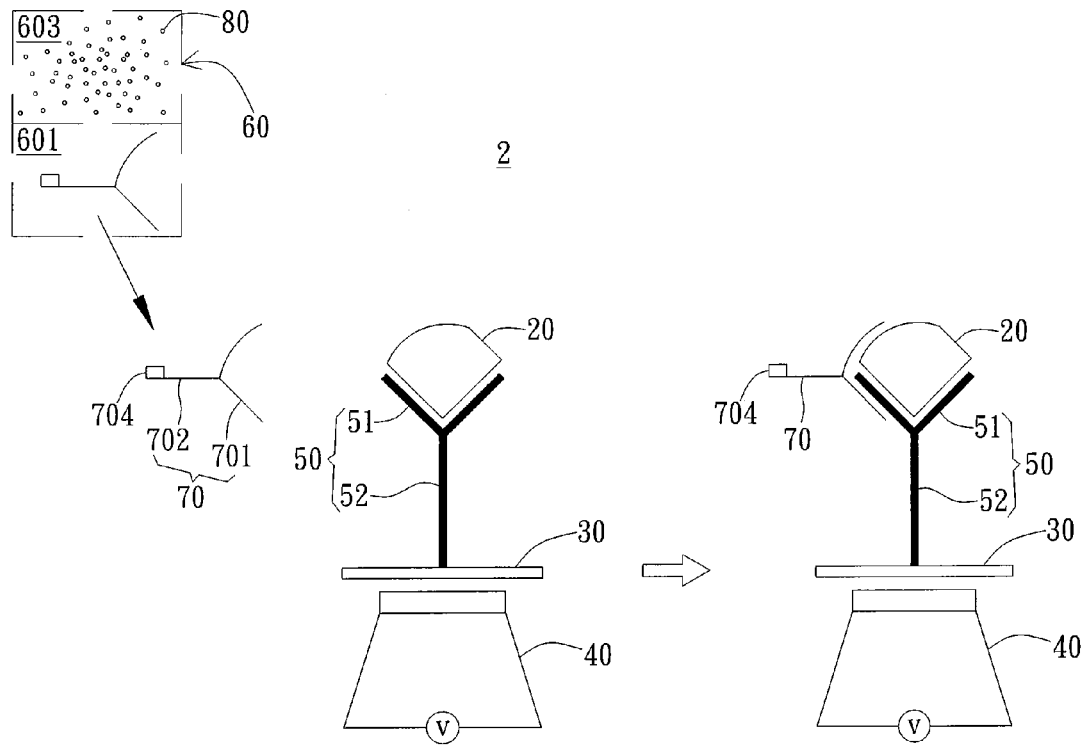
FIG. 2A is a schematic view of the reaction in the biochemical device.

As shown in an embodiment of FIG. 2A, a biochemical device 2 employing the biochemical detection unit preferably includes a releasing unit 60. In the present embodiment, the releasing unit 60 includes a first containing space 601 and a second containing space 603. However, the releasing unit 60 is not limited to including only two containing spaces; the releasing unit 60 may include only a single containing space or may include more than one containing spaces. For instance, if there is only a single containing space, the single containing space may contain different materials in supply for reactions. In the present embodiment, the releasing unit 60 is preferably a controllable agent importing device, wherein the mentioned containing space thereof can be controlled through the built-in chip of the biochemical device 2. The specifics of the control include controlling the time of opening the containing space, controlling the manner in which the contents in the containing space are released, as well as controlling the sequence in which various containing spaces are independently opened. As shown in the embodiment of FIG. 2A, the first containing space 601 contains a first affinity agent 70 while the second containing space 603 contains a luminescence-reactive agent 80. The first affinity agent 70 has a binding portion 701 and a reaction portion 702. In a preferred embodiment, the first affinity agent 70 is another anti-body, wherein the antibody can preferably bind exclusively to the receptor 50. However, in other embodiments, the first affinity agent 70 may not necessarily be an anti-body, but could in fact also be an amino acid sequence or protein with exclusive affinity attraction to the receptor 50. In the present embodiment, the containing space is preferably a chamber of the agent importing device. However, in other embodiments (not shown), the releasing unit 60 may be a controllable time-release capsule, wherein the first containing space 601 and the second containing space 603 may contain microcapsules with identical or non-identical dissolution times. In the capsule embodiment, the releasing unit 60 is also controllable in the same manner as the control form mentioned above, wherein the specifics of the control include controlling the time of opening the containing space, controlling the manner in which the contents in the containing space are released, as well as controlling the sequence in which various containing spaces are independently opened.

Figure 2B:
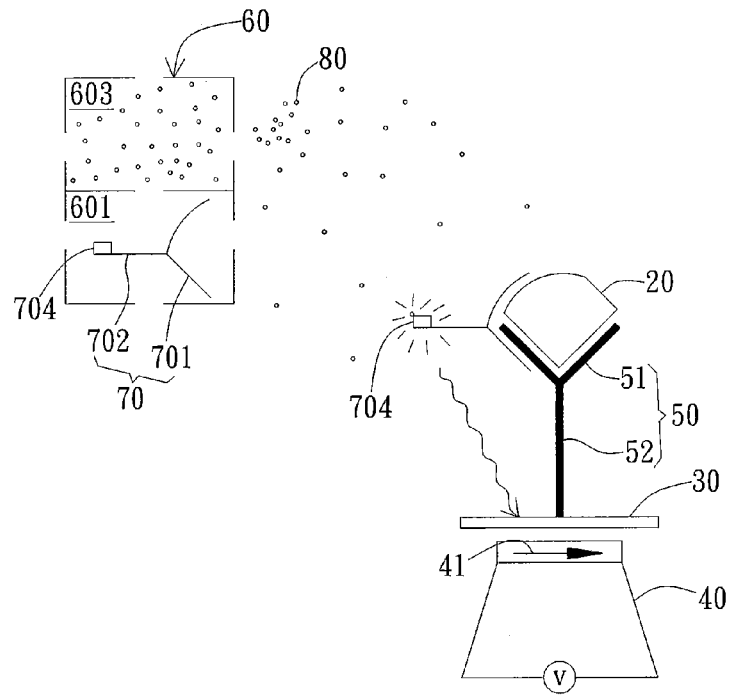
FIG. 2B is a schematic view of the embodiment of the reaction in the biochemical device.

As shown in the embodiment of FIG. 2A, the binding portion 701 of the first affinity agent 70 can bind exclusively to the affinity site 51 to which the sample 20 has been bound. As a result, the first affinity agent 70 can be prevented from binding non-exclusively to the sample 50 and consequently causing the biochemical detection unit 1 to sense a variation in resistance value in the photoconductor plate 30. In this manner of preventing the first affinity agent 70 from binding non-exclusively to the sample 50, false positive reactions may be avoided in the qualitative analysis. In addition, as shown in FIG. 2B, false positive reactions from non-exclusive binding of the first affinity agent 70 with the receptor 50 may be avoided by allowing reactions between the luminescence-reactive agent 80 (e.g., 2,2'-azino-bis(3-ethylbenzthiazoline-6-sulphonic acid) or 3,3',5,5'-Tetramethyl benzidine)) and an enzyme 704 (e.g., peroxidase) on a terminal end of the reaction portion 702 of the first affinity agent 70 to produce a fluorescence with a specific wavelength range. The above mentioned reaction is also commonly called an Enzyme-linked immunosorbent assay (ELISA). In the present embodiment, the wavelength range of the fluorescence is preferably selected from within the ranges of 620~750 nm, 495~570 nm, and 358~461 nm. However, in other embodiments, the wavelength range may be selected from 575~900 nm, 470~610 nm, and 300~480 nm. When the fluorescence mentioned above illuminates the photoconductor plate 30, the sample 20 that has definitively bonded to the affinity site 51 of the receptor 50 can be detected through the resistance change signal 41 by utilizing a suitable photoconductor in conjunction with the resistance sensing component 40. In other words, after the sample 20 binds to the receptor 50, the fluorescence resulted from the reaction of the luminescence-reactive agent 80 and the enzyme 704 can stimulate the photoconductor plate 30 and subsequently change the resistance value of the photoconductor. Due to the fact that the sample 20 is generally carried by fluid, the fluid may include but not limited to air, liquids, and semi-solids (colloid). Other than carrying the sample 20 to the receptor 50, the fluid can also carry away any first affinity agents 70 that have not been bonded to.

Figure 3:
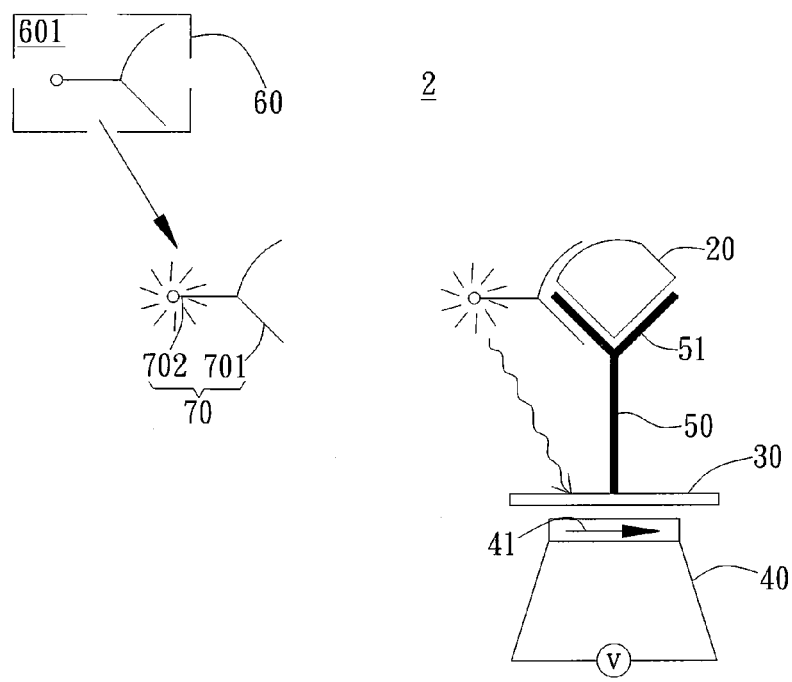
FIG. 3 is a schematic view of another embodiment of the reaction in the biochemical device.

As shown in the embodiment of FIG. 3, the biochemical device 2 with the biochemical detection unit further includes the releasing unit 60. The releasing unit 60 of the present embodiment includes the first containing space 601, wherein the first containing space 601 is the only containing space in the present embodiment. The first containing space 601 contains the first affinity agent 70 while the releasing unit 60 can control the first containing space 601 to release at least one first affinity agent 70. In the present embodiment, the first affinity agent 70 includes the binding portion 701 and the reaction portion 702, wherein the binding portion 701 binds to the affinity site 51 to which the sample 20 is already bound. In comparison to the previous embodiment, in the present embodiment, the reaction portion 702 of the first affinity agent 70 self-emits light with a specific wavelength range. More specifically, the principle of the embodiment is radio-immunoassay. In the present embodiment, the amino acid in which the isotope (e.g., $^{12}C$, $^{14}C$, $^{131}I$) is included is preferably the monomer of the reaction portion 702. However, in other embodiment the reaction portion 702 may be an amino acid sequence that binds to a specific isotope (e.g., $^{12}C$, $^{14}C$, $^{131}I$). As a result, the reaction portion 702 would become an isotopic material. In the present embodiment, if the reaction portion 702 is an isotopic material, the light wave emitted thereof would include but is not limited to $\alpha$, $\beta$, or $\gamma$ rays. However, in other embodiments, the reaction portion 702 may also be a self-luminous fluorescent protein. In the present embodiment, the range of the specific wavelength emitted from the self-luminous fluorescent protein is preferably selected from the ranges 620~750 nm, 495~570 nm and 358~461 nm. However, in other embodiments, the wavelength range is most preferably selected from the ranges 575~900 nm, 470~610 nm, and 300~480 nm. As shown in the embodiment of FIG. 3, when the light rays radiating from the reaction portion 702 hits the photoconductor plate 30, the photoconductor of the photoconductor plate 30 is stimulated, changing the resistance value as a result. The resistance sensing component 40 is then able to sense a variation in the resistance value in the photoconductor and subsequently produce the resistance change signal 41.

Figure 4:
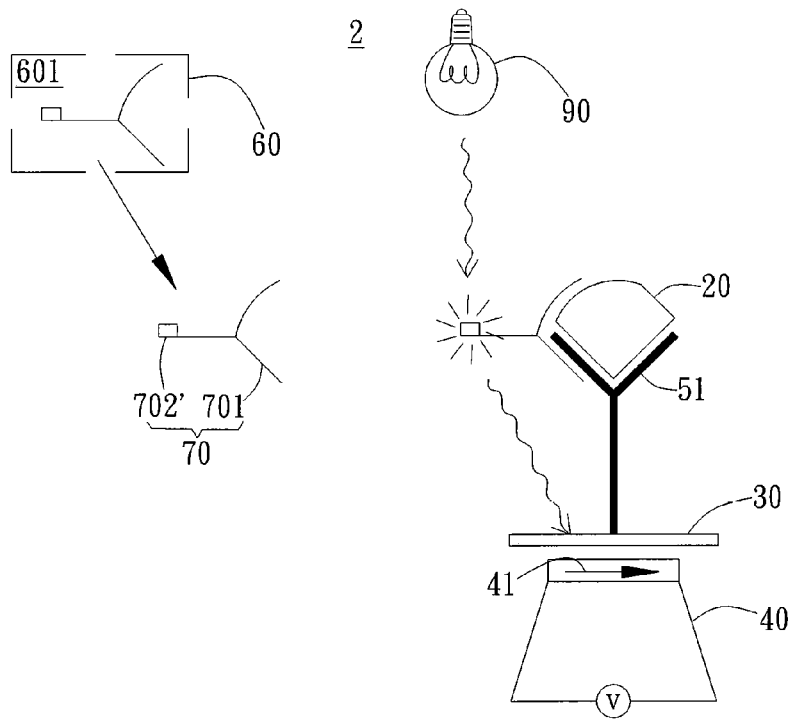
FIG. 4 is a schematic view of another embodiment of the reaction in the biochemical device.

As shown in the embodiment of FIG. 4, the biochemical device 2 with the biochemical detection unit further includes the releasing unit 60 and a light source 90. In the present embodiment, the releasing unit 60 releases at least one first affinity agent 70, wherein the first affinity agent 70 includes the binding portion 701 and a fluorescence reaction portion 702'. The binding portion 701 binds to the affinity site 51, wherein the sample 20 is already bonded to the affinity site 51. In comparison to the previous embodiment, the fluorescent reaction portion 702' can emit fluorescence light of a specific wavelength range when illuminated by the light source 90. The fluorescence light can then stimulate the photoconductor plate 30 to change the resistance value thereof. In the present embodiment, the light source 90 includes but is not limited to lasers, white light, and other monochromatic lights. In addition, the fluorescent reaction portion 702' can be designed to be fluorescent proteins radiating different wavelength ranges (e.g., green fluorescent protein GFP, red fluorescent protein HcRed, and yellow fluorescent protein ZsYellow). The specific wavelength range of the fluorescence radiating from the fluorescent reaction portion 702' is preferably selected from the ranges 620~750 nm, 495~570 nm, and 358~461 nm. However, in other embodiments, the wavelength range is most preferably selected from the ranges 575~900 nm, 470~610 nm, and 300~480 nm. Through utilizing a suitable photoconductor, the photoconductor plate 30 can change the resistance value due to the fluorescence light. The resistance sensing component 40 can then produce the resistance change signal 41.

Figure 5A:
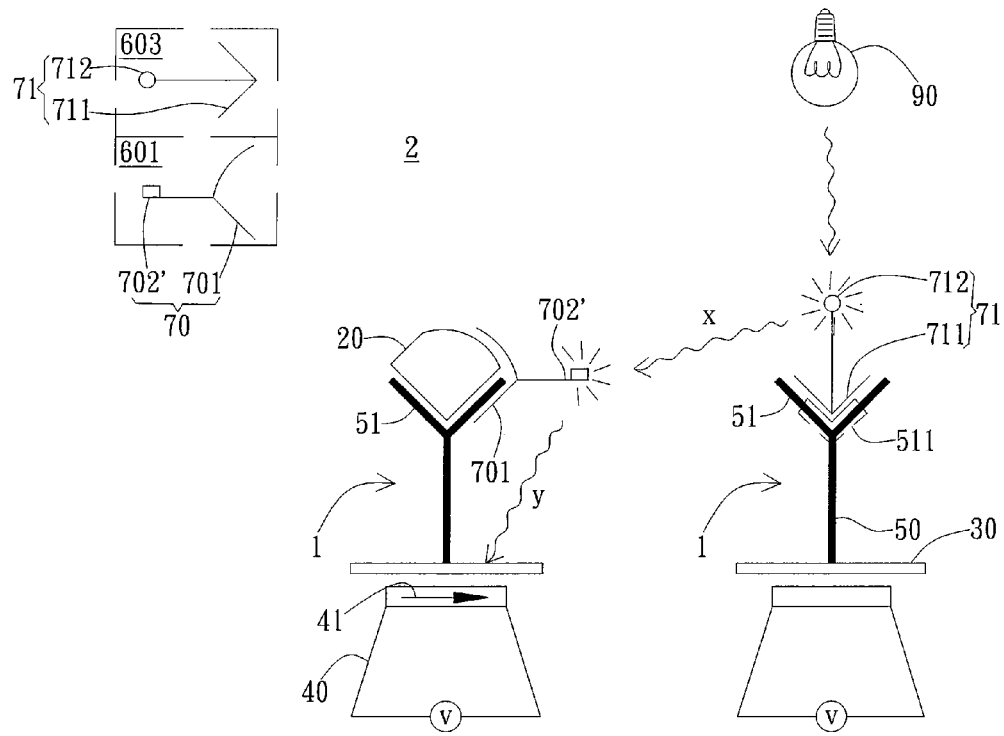
FIG. 5A is a schematic view of the embodiment of the reaction in the biochemical device to prevent false positive reactions.

In qualitative analyses, false positive reactions often result in erroneous estimations. In order to reduce the occurrence of false positive reactions, as shown in FIG. 5A, another embodiment of the present invention is provided. As shown in FIG. 5A, the biochemical device 2 with the biochemical detection unit includes the first containing space 601 and the second containing space 603. The first containing space 601 contains the first affinity agent 70, wherein the first affinity agent 70 includes the first binding portion 701 and the first fluorescent reaction portion 702'. The second containing space 603 contains a second affinity agent 71, wherein the second affinity agent 71 includes a second binding portion 711 and a second fluorescent reaction portion 712. The first binding portion 701 binds exclusively to the affinity site 51, wherein the sample 20 has already bonded to the affinity site 51. The second binding portion 711 binds exclusively to a blocking site 511, wherein the blocking site 511 is defined as a part of the receptor 50 which covers the sample 20 that is bonded to the affinity site 51. In the present embodiment, the biochemical device 2 with the biochemical detection unit further includes the light source 90. In the present embodiment, the light wavelength radiated from the light source 90 is identical to the above mentioned description of the light source 90. After the second affinity agent 71 has bonded to the blocking site 511 and the light emitted from the light source 90 illuminates the second fluorescent reaction portion 712, the second fluorescent reaction portion 712 emits a fluorescence x having a first wavelength range. In the adjacent biochemical detection unit 1, the first binding portion 701 of the first affinity agent 70 binds to the affinity site 51, wherein the sample 20 has already bonded to the affinity site 51. The first fluorescent reaction portion 702' will emit a fluorescence y having a second wavelength range after being stimulated by the fluorescence x having the first wavelength range. In turn, the fluorescence y further stimulates the photoconductor to change the resistance value of the photoconductor plate 30 to produce the resistance change signal 41. Since only one of two adjacent biochemical detection units 1 can produce resistance change signal 41, therefore the case where both adjacent biochemical detection units 1 produce the resistance change signal 41 as false positive reactions can be eliminated. Since the distance between the affinity site 51 and the photoconductor 30 affects the illumination levels of the fluorescence y having the second wavelength range on the photoconductor plate 30 that is connected to the second affinity agent 71, under weak illumination the biochemical detection unit 1 that is connected to the second agent 71 will not produce the resistance change signal 41. In addition, in other embodiments (not shown), a polarizer for filtering the fluorescence y having the second wavelength range may also be disposed between the adjacent biochemical detection units 1. In this manner, the fluorescence y having the second wavelength range can only produce reactions in the biochemical detection unit 1 connected to the first affinity agent 70. Hence, the case where false positive reactions resulting from both the adjacent biochemical detection units 1 producing the resistance change signal 41 can be eliminated. In the present embodiment, the first wavelength range of the fluorescence x and the second wavelength range of the fluorescence y are preferably selected from the ranges 620~750 nm, 495~570 nm and 358~461 nm. However, in other embodiments, the first and second wavelength ranges may most preferably be selected from the ranges 575~900 nm, 470~610 nm, and 300~480 nm, wherein the first wavelength range and the second wavelength range should not overlap. For instance, if the fluorescence x has the first wavelength range of 620~750 nm, the fluorescence y may have the second wavelength range of 495~570 nm or 358~461 nm.

Figure 5B:
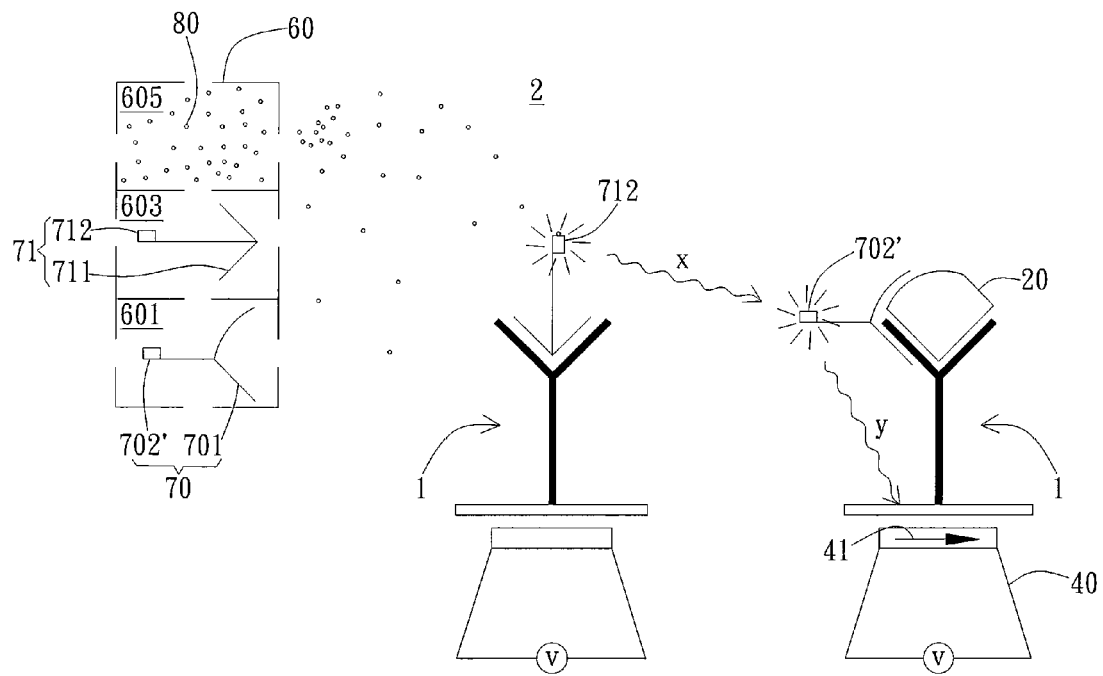
FIG. 5B is a schematic view of another embodiment of the reaction in the biochemical device to prevent false positive reactions.

As shown in another embodiment of FIG. 5B, the releasing unit 60 of the biochemical device 2 with the biochemical detection unit includes the first containing space 601, the second containing space 603, and a third containing space 605. The first containing space 601 contains the first affinity agent 70. The second containing space 603 contains the second affinity agent 71 while the third containing space 605 contains at least one luminescence-reactive agent 80. When the first affinity agent 70 and the second affinity agent 71 bind to the biochemical detection units 1 as mentioned in the prior embodiment, the at least one luminescence-reactive agent 80 released from the releasing unit 60 diffuses gradually and reacts with the second fluorescent reaction portion 712 to emit the fluorescence x having the first wavelength range. The fluorescence x having the first wavelength will further stimulate the first fluorescent reaction portion 702' to emit the fluorescence y having the second wavelength range. In the present embodiment, the case where false positive reactions resulting from both the adjacent biochemical detection units 1 producing the resistance change signal 41 can be eliminated. However, in the present embodiment, the luminescence-reactive agent 80—not the light source 90—is provided as the source of the fluorescence stimulations. As shown in the embodiment in FIG. 5B, the first wavelength range of the fluorescence x and the second wavelength range of the fluorescence y are preferably selected from the ranges 620~750 nm, 495~570 nm and 358~461 nm. However, in other embodiments, the first and second wavelength ranges may most preferably be selected from the ranges 575~900 nm, 470~610 nm, and 300~480 nm, wherein the first wavelength range and the second wavelength range do not overlap.

Figure 6A:
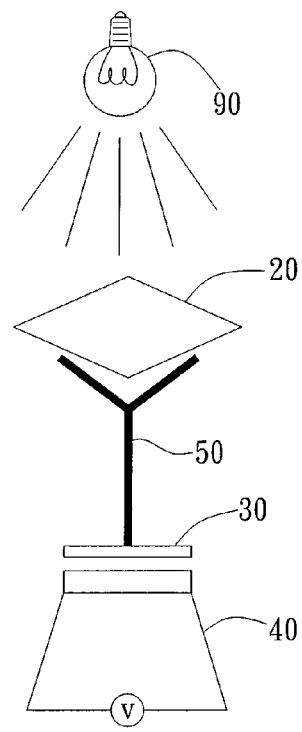
FIG. 6A is a schematic view of the embodiment of the blocking in the biochemical device.
Figure 6B:
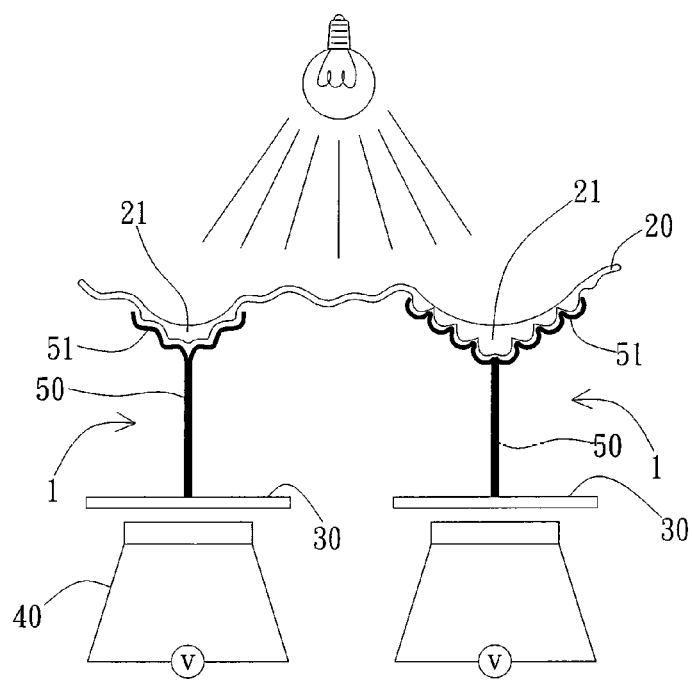
FIG. 6B is a schematic view of another embodiment of the blocking in the biochemical device.

As shown in the embodiment of FIG. 6A, the biochemical detection unit 1 for detecting the sample 20 includes the light source 90, the photoconductor plate 30, the receptor 50, and the resistance sensing component 40. The light source 90 illuminates the receptor 50 and the photoconductor plate 30. In the present embodiment, the affinity site 51 of the receptor 50 can bind to the sample 20 having larger size. The sample 20 having larger size will consequently block the light so that the photoconductor plate 30 would not be illuminated, and hence the resistance change signal 41 would not be produced. As shown in the embodiment of FIG. 6B, different epitopes 21 of the sample 20 separately bind to the affinity sites 51 of the receptors 50 of the adjacent biochemical detection units 1. However, if the adjacent biochemical detection units 1 are designed to bond with large-sized sample 20 having different epitopes 21, a light blocking effect would be produced and light from the light source 90 would be blocked by the large-sized sample 20. In comparison to the embodiment of FIG. 6A, blocking effects resulting from non-exclusive binding between the affinity site 51 and materials other than sample 20 can be reduced. In effect, false negative reactions can be subsequently reduced.

As mentioned above, the biochemical detection unit 1 of the present invention includes the photoconductor plate 30, the receptor 50, and the resistance sensing component 40. A Detection chip (also known as a Biochip) may be formed through gathering a plurality of biochemical detection units 1. The biochip preferably is made of $10^6$~$10^{12}$ biochemical detection units 1. However, in other embodiments, the quantity of the biochemical detection units 1 is not limited to $10^6$~$10^{12}$ units. In the preferred embodiment of the biochip, the design of the biochemical detection units 1 is different.

Figure 7A:
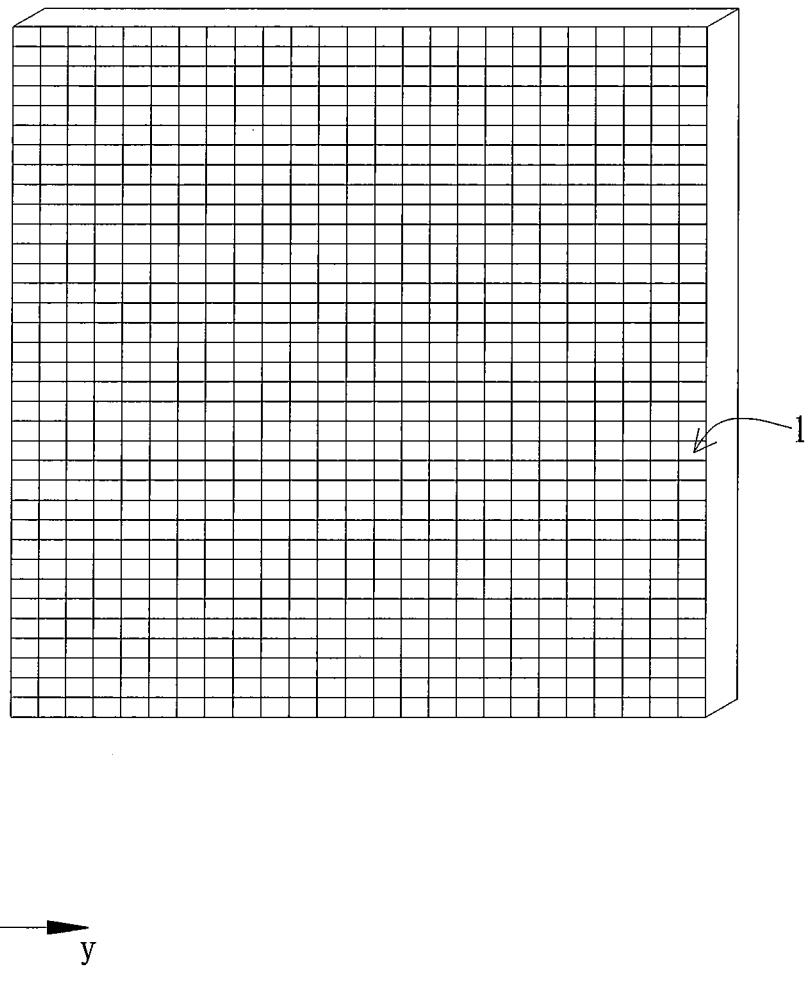
FIG. 7A is a schematic view of the biochip.
Figure 7B:
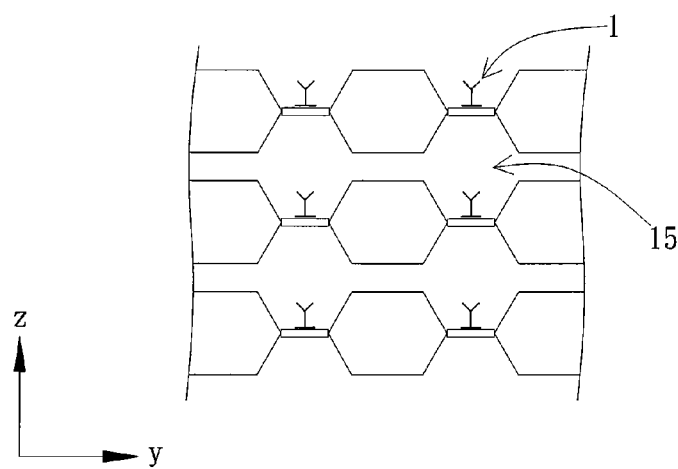
FIG. 7B is a schematic view of the embodiment of the biochip in Z axis.
Figure 7C:
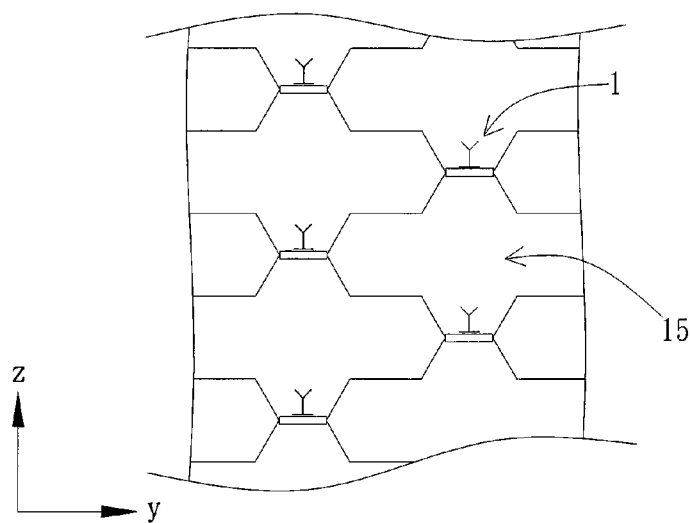
FIG. 7C is a schematic view of another embodiment of the biochip in Z axis.
Figure 7D:
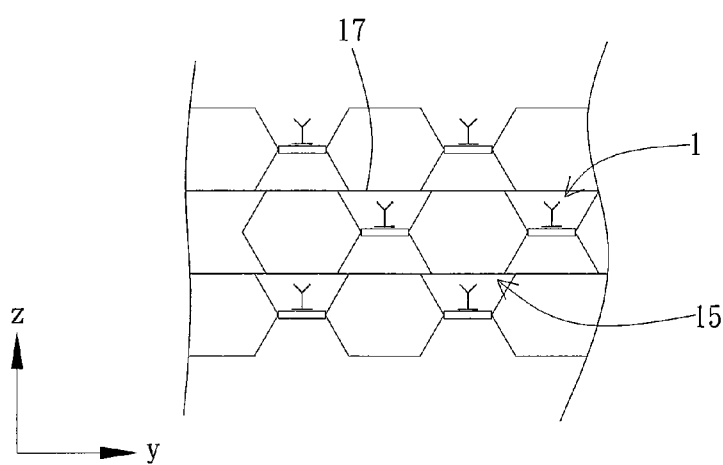
FIG. 7D is a schematic view of another embodiment of the biochip in Z axis.

For instance, as shown in the embodiment of FIG. 6B, adjacent biochemical detection units 1 are different. As shown in FIG. 7A, the biochip is made up of a plurality of biochemical detection units 1. In addition, as shown in FIG. 7B, the biochemical detection units 1 are arranged in top-down order on the Z axis. A reaction space 15 exists between every column of biochemical detection units 1, wherein the reaction space 15 is provided to receive the fluid carrying the sample 20. The fluid may include air, liquid, and semi-solid (colloid). When the fluid carries the sample 20 to the biochemical detection unit 1, the sample 20 will bind exclusively to the receptor 50. As shown in the embodiments of FIGS. 7C and 7D, there may be other ways to arrange the biochemical detection units 1. As shown in FIG. 7C, the biochemical detection units 1 are arranged in an interlaced manner. The interlaced arrangement can increase the space of the reaction space 15 while simultaneously prevent the biochemical detection units 1 from being overly close to each other and causing false positive reactions. As shown in FIG. 7D, the closed arrangement of the biochemical detection units 1 can reduce the volume of the biochip so that the biochip can be more portable. Since the biochemical detection units 1 are overly close in FIG. 7D, a closure lid 17 is required to be disposed. The closure lid 17 is preferably disposed on top of each row of the biochemical detection unit 1 to prevent false positive reactions that may be caused by the scattering of the fluorescence. However, the closed arrangement reduces the space of the reaction space 15. Therefore, the closed arrangement is more suitable for relatively more sensitive biochemical detection units 1 or for fluids carrying large quantities of samples.

Figure 7E:
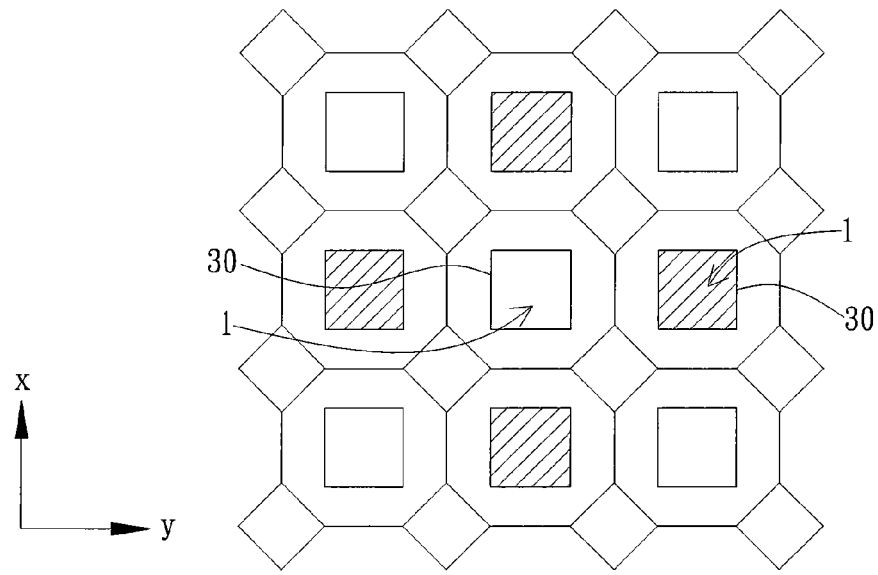
FIG. 7E is a schematic view of the embodiment of the biochip in X-Y axis.
Figure 7F:
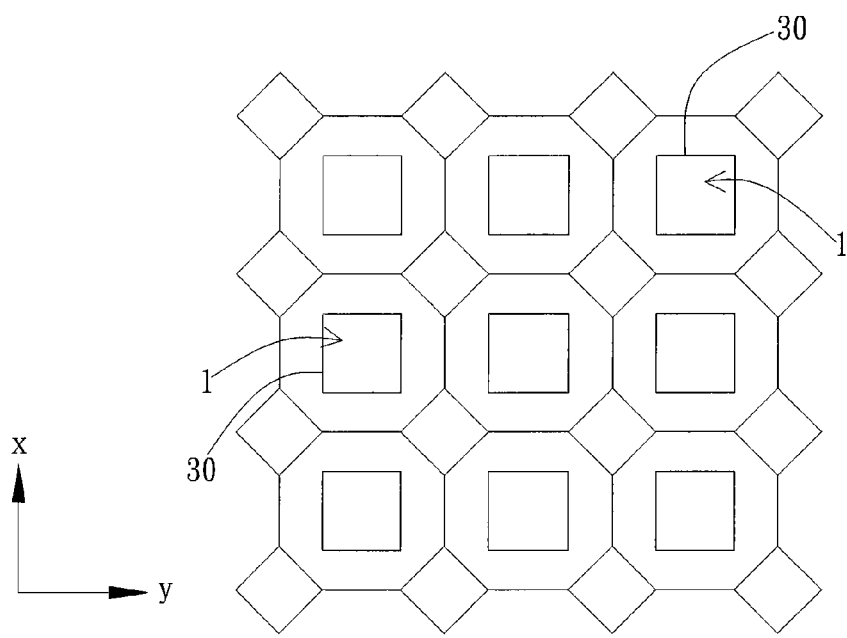
FIG. 7F is a schematic view of another embodiment of the biochip in X-Y axis.

As shown in the embodiments of FIGS. 7E and 7F, in terms of the X-Y plane, the arranged photoconductor plates 30 does not necessarily need to be made of identical materials. As shown in the embodiment of FIG. 7E, the photoconductor plates 30 are composed of different materials that are arranged in alternating fashion. The alternating arrangement shown in FIG. 7E can further prevent false positive reactions that may be caused by the scattering of the fluorescence. The reason behind this is that scattered fluorescence cannot stimulate other photoconductor plates 30 due to its frequency. Furthermore, the illumination level on each photoconductor plate 30 by the scattered fluorescence is different. Therefore, as a result of the low illumination, photoconductor plates 30 that are too far away will not be sensed by the resistance sensing component 40 even if the low illumination is enough to stimulate the photoconductor plates 30.

Figure 8:
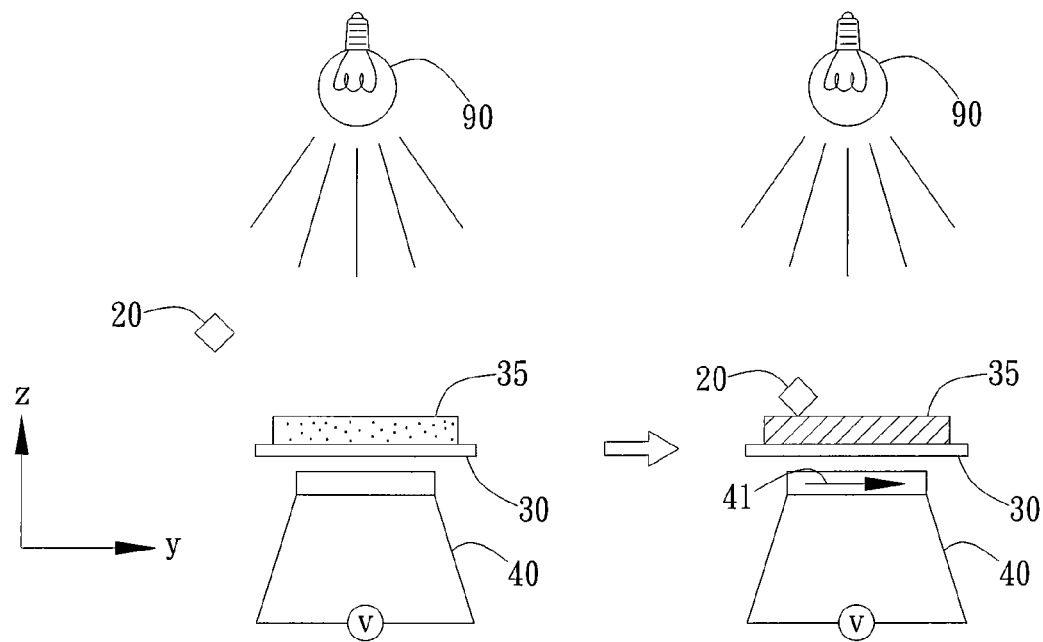
FIG. 8 is a schematic view of the embodiment of the biochip discoloring.

As shown in the embodiment of FIG. 8, the biochemical detection unit 1 for detecting sample 20 includes the light source 90, the photoconductor plate 30, an agent 35, and the resistance sensing component 40, wherein the agent 35 is disposed on the photoconductor plate 30. When the sample 20 comes in contact with the agent 35, the agent 35 will produce a chemical reaction and change colors. Since any change in color of the agent 35 will affect the illumination levels of the light radiated from the light source 90, the illumination on the photoconductor plate 30 will be reduced. Due to the fact that the illumination levels have changed, the resistance sensing component 40, with help from the electrically coupled photoconductor plate 30, will produce the resistance change signal 41. In the present embodiment, since the agent 35 is disposed directly on top of the photoconductor plate 30, the agent 35 can also be regarded as one type of the receptor 50. Although the agent 35 of the present embodiment generally has exclusive affinity to the sample 20, in other embodiments however, the agent 35 may react to the sample 20 without necessarily having exclusive affinity. The agent 35 can be designed to be able to react with a specific compound or a specific functional group, and therefore the agent 35 can detect single compounds as well as specific compound derivatives.

Figure 9A:
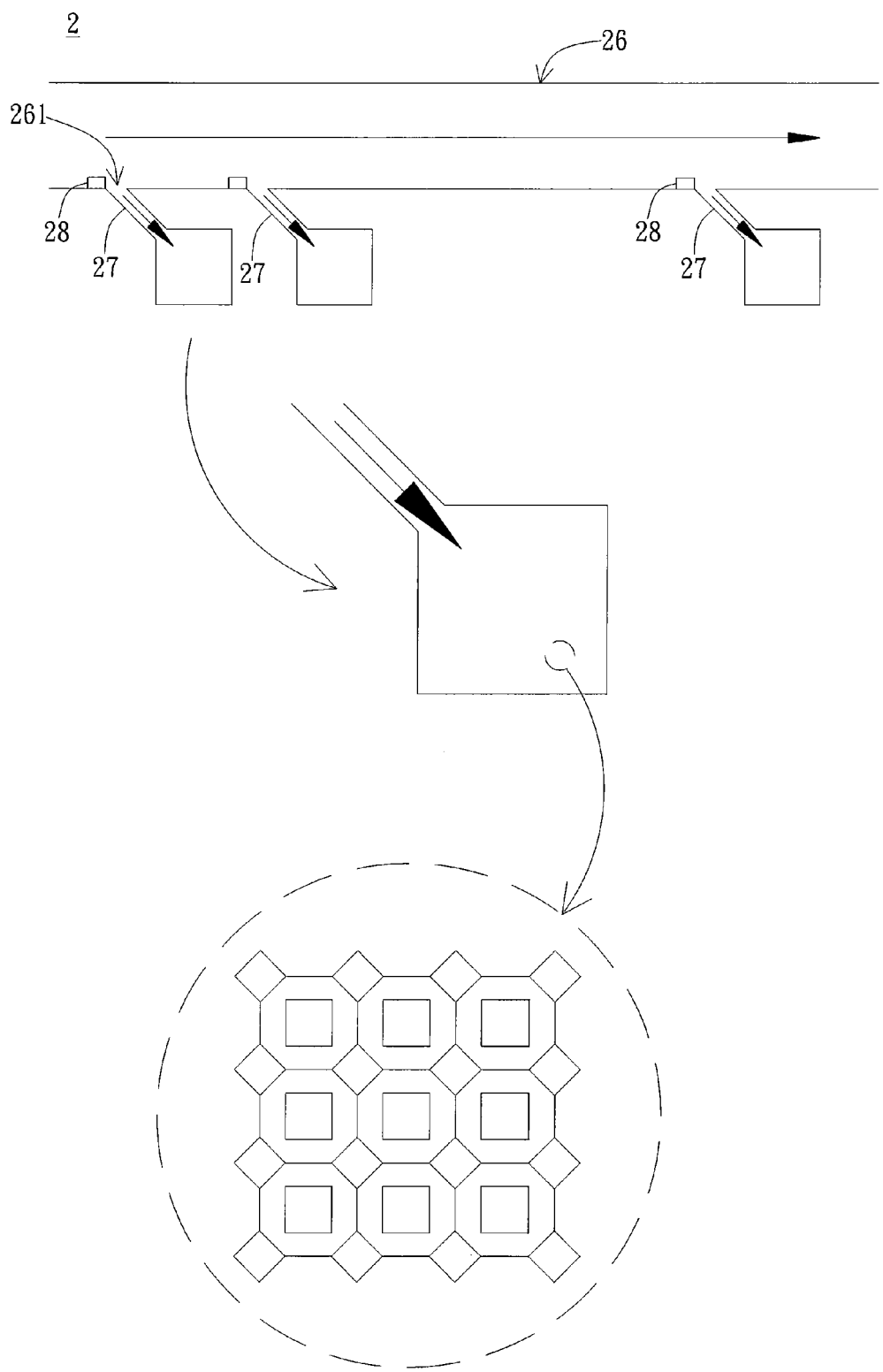
FIG. 9A is a schematic view of the embodiment of the sampling unit of the biochemical device.

As shown in an embodiment in FIG. 9A, the biochemical device 2 with the biochemical detection unit further includes a primary channel 26, at least a sub-channel 27, and a sampling unit 28. The sub-channel 27 communicates with the primary channel 26 through an opening 261. In the present embodiment, the photoconductor plate 30 is disposed at an end of the sub-channel 27. However, in other embodiments (not shown), the photoconductor plate 30 is disposed in the sub-channel 27 or the primary channel 26. Since the biochemical device 2 has the sampling unit 28 disposed by the opening 261, the sampling unit 28 can selectively allow the sample 20 to enter the sub-channel 27. As a result, if the concentration of sample 20 gets too high and causes oversaturation to occur, the sampling unit 28 can selectively refuse entry for the sample 20 into the sub-channel 27. In this manner, oversaturation due to the reaction between the sample 20 and the biochemical detection unit 1 will not occur and subsequently, the biochemical device 2 with the biochemical detection unit can accomplish the quantitative analysis. As shown in the embodiment of FIG. 9A, the sampling unit 28 is a valve, wherein the sampling unit 28 in valve form is electrically connected to the resistance sensing component 40. When the bonding or color-changing reaction between the sample 20 and the biochemical detection unit 1 at the end of the sub-channel 27 trends toward oversaturation levels, the resistance sensing component 40 will sense the resistance value varying over a default value and then output a control signal to the sampling unit 28 in valve form to close the opening 261. Consequently, the sampling unit 28 in valve form of the present invention can prevent reaction oversaturation of the sample 20 and the biochemical detection unit 1, and thus the present invention can accomplish the requirement for quantitative analysis.

Figure 9B:
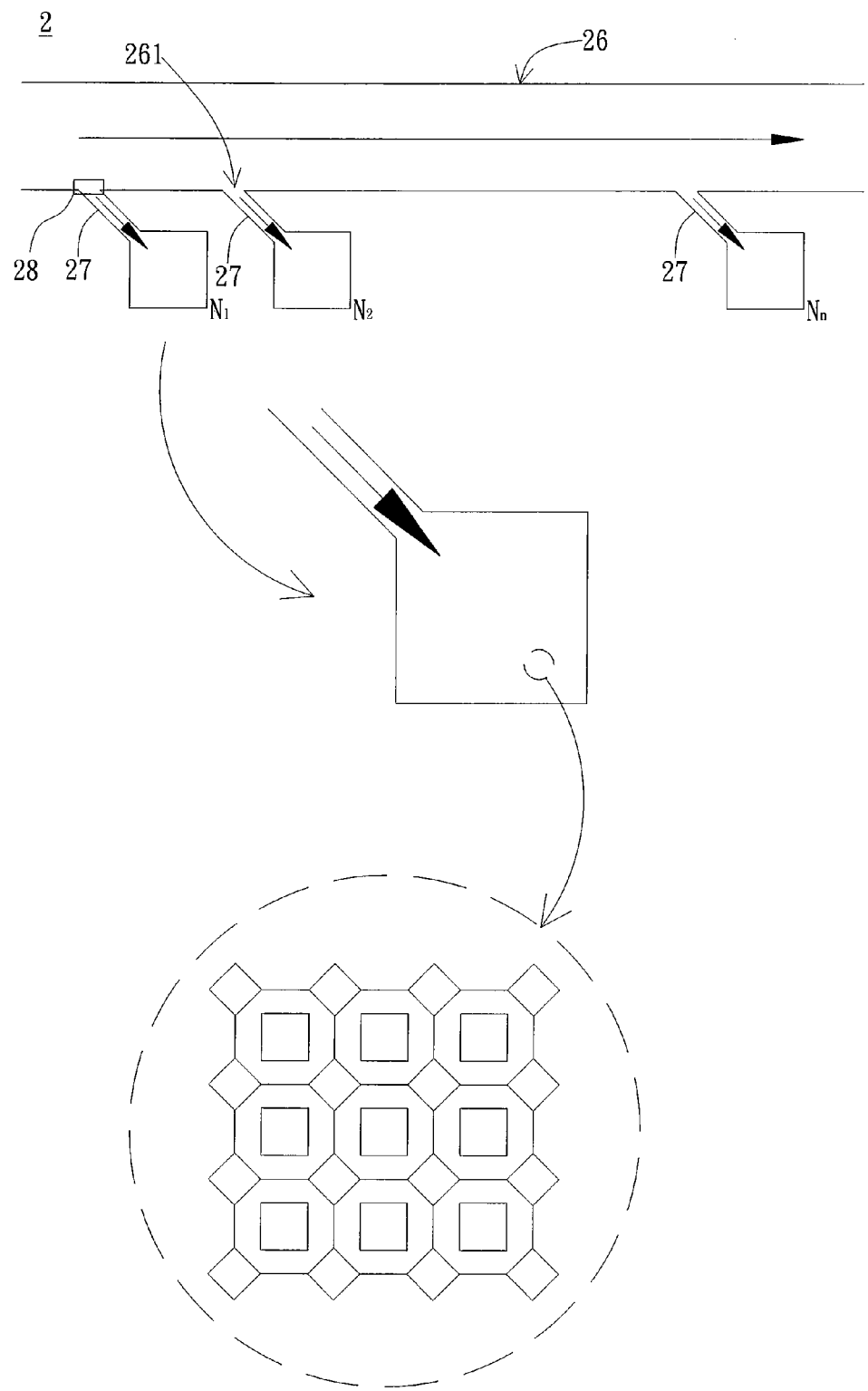
FIG. 9B is a schematic view of another embodiment of the sampling unit of the biochemical device.

As shown in an embodiment in FIG. 9B, the biochemical device 2 with the biochemical detection unit includes the primary channel 26 and a plurality of sub-channels 27 such as N1, N2, . . . , Nn. The connecting spot between each of the sub-channels 27 and the primary channel 26 is the opening 261. In the present embodiment, the sampling unit 28 is preferably disposed at the opening 261, wherein the sampling unit 28 can be an electrode set which can produce dielectrophoretic forces. The dielectrophoretic force produced by the sampling unit 28 in electrode set form can be applied to sieve the suitable sample 20 to enter the sub-channel 27. The dielectrophoretic force can selectively allow the sample 20 to enter the sub-channel 27 and get to the end of the sub-channel 27 to react with the biochemical detection unit 1. However, in other embodiments, the sampling unit 28 can be an optical tweezers for segregating various samples 20. The sampling unit 28 in optical tweezers form can be used in the present invention to selectively allow the sample 20 to enter the sub-channel 27, and therefore avoid oversaturation.

Figure 9C:
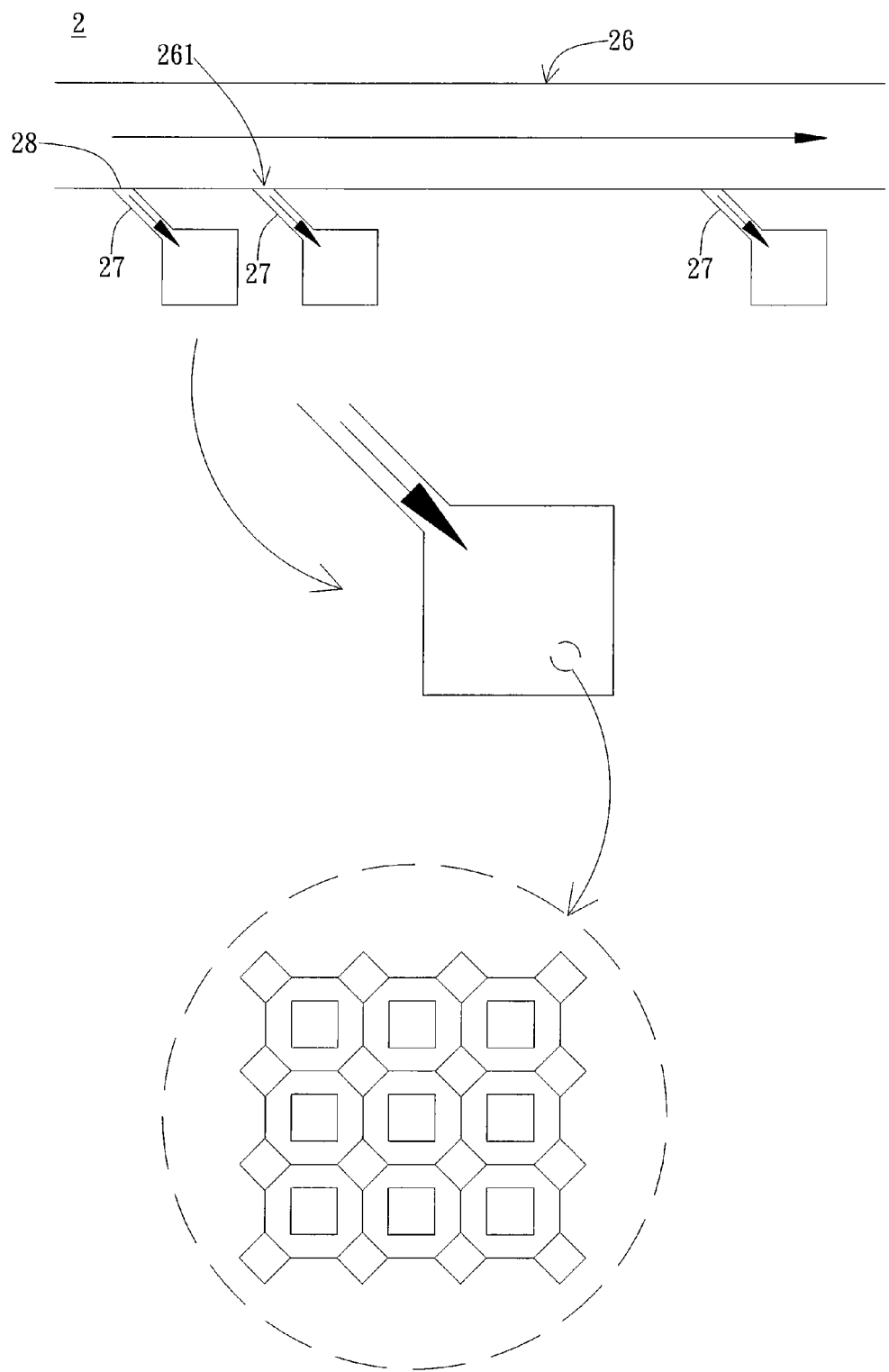
FIG. 9C is a schematic view of another embodiment of the sampling unit of the biochemical device.

As shown in an embodiment in FIG. 9C, the opening 261 is formed at the joint of the primary channel 26 and the sub-channel 27 of the biochemical device 2. In the present embodiment, the sampling unit 28 is a semi-transparent membrane disposed at the opening 261. The sampling unit 28 in semi-transparent membrane form is selectively permeable for various differing sizes of the samples 20 and can affect the concentration of the sample 20 in the sub-channel 27 based on the osmotic pressure caused by the sample 20. As a result, the concentration of the sample 20 in the sub-channel 27 will reach a steady state so that the occurrence of oversaturation may be avoided. Therefore the present invention achieves the requirement for quantitative analysis.

Although the preferred embodiments of present invention have been described herein, the above description is merely illustrative. The preferred embodiments herein disclosed do not in any way limit the scope of the present invention. Further modification of the invention herein disclosed will occur to those skilled in the respective arts and all such modifications are deemed to be within the scope of the invention as defined by the appended claims.

What is claimed is:

1. A biochemical device, including:
a biochemical detection unit for detecting a sample having at least one epitope for reacting with the biochemical detection unit, including:
a photoconductor plate;
at least one receptor disposed on the photoconductor plate by a bond, the receptor comprising an affinity site for binding specifically to the sample, being variable in conformation and able to produce a conformational change in response to binding to the sample, wherein the conformational change weakens the bond between the receptor and the photoconductor plate and results in the receptor being separated from the photoconductor plate when bound to the sample;
a resistance sensing component, electrically coupled to the photoconductor plate, for sensing a variation in resistance value of the photoconductor plate, wherein the separation of the receptor from the photoconductor plate causes the variation in resistance value of the photoconductor plate;
a light source for illuminating the receptor and the photoconductor, wherein the sample bound to the affinity site of the receptor blocks light from the light source to the photoconductor plate and causes the variation in resistance value of the photoconductor plate; and
a primary channel for the sample entering first and at least one sub-channel for the sample entering later on;
wherein the at least one sub-channel communicates with the primary channel through an opening, wherein the photoconductor plate is disposed in the primary channel or the sub-channel, at least one portion of the sample from the primary channel enters at least one sub-channel towards the photoconductor plate; and
a sampling unit, disposed by the opening and electrically connected to the resistance sensing component, for selectively allowing the sample to enter the sub-channel upon concentration of the sample, wherein the resistance sensing component outputs a control signal to the sampling unit for the sampling unit closing the opening when the resistance sensing component senses the resistance value varying over a default value.

2. The biochemical device of claim 1, wherein the sampling unit includes a semi-transparent membrane.

3. The biochemical device of claim 1, wherein the sampling unit includes a valve, the valve is electrically connected to the resistance sensing component, the resistance sensing component outputs a control signal to the valve for the valve closing the opening when the resistance sensing component senses the resistance value varying over a default value.

4. The biochemical device of claim 1 further comprising a controllable agent importing device disposed externally to the biochemical detection unit, comprising at least one containing space and releasing at least one agent to react with the receptor bound to the sample to cause the variation in resistance value;
wherein the biochemical device in sequence has the affinity site binding to the sample and the controllable agent importing device releasing the at least one agent; wherein an opening time and a sequence of opening of the controllable agent importing device are controlled so as to release the at least one agent from the at least one containing space after the sample bound to the affinity site.

5. The biochemical device of claim 4, wherein the at least one agent includes at least one affinity agent having a binding portion for binding to the affinity site being already bound to the sample and a reaction portion, wherein the releasing unit further releases at least one luminescence-reactive agent, a fluorescence having a specific wavelength range is produced and emitted after the luminescence-reactive agent reacting with the reaction portion, the fluorescence stimulates the photoconductor plate and causes the variation in resistance value of the photoconductor plate.

6. The biochemical device of claim 5, wherein the specific wavelength range is selected from 620~750 nm, 495~570 nm, and 358~461 nm.

7. The biochemical device of claim 4, wherein the at least one agent includes at least one affinity agent having a binding portion for binding to the affinity site being already bound to the sample and a reaction portion for self-emitting a light having a specific wavelength range, the light stimulates the photoconductor plate and causes the variation in resistance value of the photoconductor plate.

8. The biochemical device of claim 7, wherein the specific wavelength range is selected from 620~750 nm, 495~570 nm, and 358~461 nm.

9. The biochemical device of claim 4 wherein the at least one agent includes at least one affinity agent having a binding portion for binding to the affinity site being already bound to the sample and a fluorescent reaction portion for emitting a fluorescence having a specific wavelength range after being illuminated by light from the light source, the fluorescence stimulates the photoconductor plate and causes the variation in resistance value of the photoconductor plate.

10. The biochemical device of claim 9, wherein the specific wavelength range is selected from 620~750 nm, 495~570 nm, and 358~461 nm.

11. The biochemical device of claim 4, wherein the at least one agent includes a first affinity agent and a second affinity agent, the first affinity agent comprises a first binding portion for binding specifically to the affinity site being already bound to the sample and a first fluorescent reaction portion, the second affinity agent comprises a second binding portion for binding specifically to a blocking site of the receptor and a second fluorescent reaction portion, the second fluorescent reaction portion emits a fluorescence having a first wavelength range after being illuminated by light from the light source, the fluorescence having the first wavelength range excites the first fluorescent reaction portion to produce a fluorescence having a second wavelength range to further stimulate the photoconductor plate and cause the variation in resistance value of the photoconductor plate.

12. The biochemical device of claim 11, wherein the first wavelength range and the second wavelength range are selected from 620~750 nm, 495~570 nm, and 358~461 nm, and the first wavelength range does not overlap the second wavelength range.

13. The biochemical device of claim 4, wherein the at least one agent includes a first affinity agent, a second affinity agent, and at least one luminescence-reactive agent, the first affinity agent comprises a first binding portion for binding specifically to the affinity site being already bound to the sample and a first fluorescent reaction portion, the second affinity agent comprises a second binding portion for binding specifically to a blocking site of the receptor and a second fluorescent reaction portion, a fluorescence having a first wavelength range is produced and emitted after the luminescence-reactive agent reacting with the second fluorescent reaction portion, the first fluorescence having the first wavelength range excites the first fluorescent reaction portion to produce a fluorescence having a second wavelength range to further stimulate the photoconductor plate and causes the variation in resistance value of the photoconductor plate.

14. The biochemical device of claim 13, wherein the first wavelength range and the second wavelength range are selected from 620~750 nm, 495~570 nm, and 358~461 nm, and the first wavelength range does not overlap the second wavelength range.

* * * * *